(12) United States Patent
Wächter-Stehle et al.

(10) Patent No.: US 10,043,270 B2
(45) Date of Patent: Aug. 7, 2018

(54) IMAGE PROCESSING APPARATUS AND METHOD FOR SEGMENTING A REGION OF INTEREST

(71) Applicant: KONINKLIJKE PHILIPS N.V., Eindhoven (NL)

(72) Inventors: Irina Wächter-Stehle, Hamburg (DE); Juergen Weese, Norderstedt (DE); Christian Buerger, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/126,626

(22) PCT Filed: Feb. 27, 2015

(86) PCT No.: PCT/EP2015/054189
§ 371 (c)(1),
(2) Date: Sep. 16, 2016

(87) PCT Pub. No.: WO2015/139937
PCT Pub. Date: Sep. 24, 2015

(65) Prior Publication Data
US 2017/0084023 A1    Mar. 23, 2017

(30) Foreign Application Priority Data
Mar. 21, 2014  (EP) .................................... 14161050

(51) Int. Cl.
*G06T 7/00* (2017.01)
*A61B 8/00* (2006.01)
(Continued)

(52) U.S. Cl.
CPC .......... *G06T 7/0012* (2013.01); *A61B 8/4494* (2013.01); *A61B 8/483* (2013.01);
(Continued)

(58) Field of Classification Search
None
See application file for complete search history.

(56) References Cited

U.S. PATENT DOCUMENTS 7,672,492 B2   3/2010  Shen et al.
8,023,703 B2   9/2011  Franaszek et al.
(Continued)

FOREIGN PATENT DOCUMENTS

DE       10111661 A1    12/2002
WO       02073536 A2     9/2002
(Continued)

OTHER PUBLICATIONS

Ecabert, et al, "Automatic Model-Based Segmentation of the Heart in CT images," IEEE Transactions on Medical Imaging, vol. 27(9), p. 1189-1201, 2008 (Abstract).
(Continued)

*Primary Examiner* — Bobbak Safaipour (57) ABSTRACT

An image processing apparatus (16) is disclosed for segmenting a region of interest (15) in a multi-dimensional image data of an object (12). The image processing apparatus comprises an interface for receiving an image data of the object including the region of interest to be segmented. A selection unit selects a deformable model 30 of an anatomical structure corresponding to the object in the image data. A processing unit segments the region of interest by adapting the deformable model on the basis of the image data (xt) and additional information of the object.

12 Claims, 6 Drawing Sheets

(51) Int. Cl.
  *G06T 7/12*    (2017.01)
  *G06T 7/149*   (2017.01)
  *G06T 7/11*    (2017.01)
  *A61B 8/08*    (2006.01)
  *G06T 7/20*    (2017.01)
  *G06T 7/60*    (2017.01)

(52) U.S. Cl.
  CPC .............. *A61B 8/5215* (2013.01); *A61B 8/54* (2013.01); *G06T 7/11* (2017.01); *G06T 7/12* (2017.01); *G06T 7/149* (2017.01); *G06T 7/20* (2013.01); *G06T 7/60* (2013.01); *G06T 2207/10076* (2013.01); *G06T 2207/20116* (2013.01); *G06T 2207/20124* (2013.01); *G06T 2207/30004* (2013.01); *G06T 2207/30016* (2013.01); *G06T 2207/30048* (2013.01); *G06T 2207/30056* (2013.01)

(56) References Cited

U.S. PATENT DOCUMENTS

| | | | | |
|---|---|---|---|---|
| 8,144,950 B2* | 3/2012 | Peters | ...................... | G06T 9/001 382/128 |
| 8,150,116 B2* | 4/2012 | Zhou | ...................... | G06K 9/0055 382/128 |
| 9,532,762 B2* | 1/2017 | Cho | ...................... | A61B 6/502 |
| 2003/0158855 A1* | 8/2003 | Farnham | ............... | G06F 3/0481 |
| 2006/0008143 A1 | 1/2006 | Truyen et al. | | |
| 2006/0228009 A1* | 10/2006 | Fidrich | ...................... | G06T 7/12 382/128 |
| 2008/0304744 A1* | 12/2008 | Peters | ...................... | G06T 9/001 382/173 |
| 2010/0121316 A1* | 5/2010 | Weese | ...................... | A61B 90/36 606/1 |
| 2012/0082354 A1* | 4/2012 | Peters | ...................... | G06T 7/12 382/128 |
| 2013/0072943 A1* | 3/2013 | Parmar | .................. | A61B 5/062 606/130 |
| 2016/0379372 A1* | 12/2016 | Groth | ...................... | G06T 7/149 382/131 |
| 2017/0330328 A1* | 11/2017 | Peters | ...................... | G06T 7/149 |

FOREIGN PATENT DOCUMENTS

| WO | 2006029037 A2 | 3/2006 |
| WO | 2007072363 A2 | 6/2007 |
| WO | 2011070464 A2 | 6/2011 |

OTHER PUBLICATIONS

M. Kass et al., "Snakes: Active Contour Models", International Journal of Computer Vision, 321-331 (1988).

Dornheim, et al., Generation and Initialization of Stable 3D Mass-Spring Models for the Segmentation of the Thyroid Cartilage, Pattern Recognition Lecture Notes in Computer Science, vol. 4174, 2006, pp. 162-171 (Abstract).

* cited by examiner

IMAGE PROCESSING APPARATUS AND METHOD FOR SEGMENTING A REGION OF INTEREST

This application is the U.S. National Phase application under 35 U.S.C. § 371 of International Application No. PCT/EP2015/054189, filed on Feb. 27, 2015, which claims the benefit of European Patent Application No. 14161050.1, filed Mar. 21, 2014. These applications are hereby incorporated by reference herein.

FIELD OF THE INVENTION

The present invention relates to an image processing apparatus for segmenting a region of interest in multi-dimensional image data of an object. Further, the present invention relates to a method for segmenting a region of interest in a multi-dimensional image data of an object. The present invention further relates to a computer program for segmenting a region of interest in a multi-dimensional image data of an object. The present invention finally relates to a medical imaging system comprising an image acquisition unit.

BACKGROUND OF THE INVENTION

In the field of medical image processing, various processing tasks are typically performed on medical images like ultrasound images, MRT images, computer tomography images or the like. One specific processing task, which is a fundamental task in many image processing applications, is the segmentation of a region of interest e.g. a specific organ. The segmentation is necessary for identifying organs or for special diagnosis e.g. based on volume quantification in order to improve the determination of treatment parameters.

For many organs, the image segmentation can successfully be performed with deformable models, which are based on a mesh structure with a topology which remains unchanged during adaptation to the image being segmented. Model-based segmentation has been considered very efficient for a wide variety of simple to complex organs like bones, liver, heart with nested structures. A corresponding method for facilitating of images using deformable meshes is e.g. known from WO 2007/072363.

WO 2011/070464 A2 discloses a system and a method for automatic segmentation, performed by selecting a deformable model of an anatomical structure of interest imaged in a volumetric image, wherein the deformable model is formed of a plurality of polygons including vertices and edges, wherein a feature point of the anatomical structure of interest corresponding to each of the plurality of polygons is detected and the deformable model is adapted by moving each of the vertices toward the corresponding feature point until the deformable model morphs to a boundary of the anatomical structure of interest.

WO 2006/029037 A2 discloses a system and a method for defining and tracking a deformable shape of a candidate anatomical structure wall in a three-dimensional image, wherein the shape of the candidate anatomical structure is represented by a plurality of labeled 3D landmark points and at least one 3D landmark point of the deformable shape in an image frame is defined.

Although model-based segmentations generally provide a reliable and accurate identification and segmentation of the organs, some anatomical structures like the apex of the left ventricle of the heart, or the tip of the liver or the horn of the ventricles of the brain are often difficult to detect in the medical images so that the segmentation of these features is challenging.

SUMMARY OF THE INVENTION

It is an object of the present invention to provide an image processing apparatus and a corresponding method for segmenting a region of interest in multi-dimensional image data of an object having an improved reliability and accuracy.

According to one aspect of the present invention, an image processing apparatus is provided for segmenting a region of interest in multi-dimensional image data of an object, comprising:
an interface for receiving the image data of the object including the region of interest to be segmented,
a selection unit for selecting a deformable model of an anatomical structure corresponding to the object in the image data,
a processing unit for segmenting the region of interest by adapting the deformable model on the basis of the image data and additional anatomical information of the object.

According to another aspect of the present invention a method for segmenting a region of interest in a multi-dimensional image data of an object is provided, comprising the steps of:
receiving the image data of the object including the region of interest to be segmented,
selecting a deformable model of an anatomical structure corresponding to the object in the image data,
segmenting the region of interest by applying the deformable model to the image data, and
adapting the deformable model on the basis of the image data and additional anatomical information of the object.

According to another aspect of the invention a computer program for segmenting a region of interest in a multi-dimensional image data of an object is provided, comprising program means for causing a computer to carry out the steps:
receiving the image data of the object including the region of interest to be segmented,
selecting a deformable model of an anatomical structure corresponding to the object in the image data,
segmenting the region of interest by applying the deformable model to the image data, and
adapting the deformable model on the basis of the image data and additional anatomical information of the object when said computer program is carried out on a computer.

According to another aspect of the present invention a medical imaging system is provided comprising an image acquisition unit for acquiring medical images and comprising an image processing apparatus according to the present invention for segmenting a region of interest in the multi-dimensional image data of an object acquired by the image acquisition unit.

Preferred embodiments of the invention are defined in the dependent claims. It should be understood that the claimed method has similar and/or identical preferred embodiments as the claimed device and as defined in the dependent claims.

The present invention is based on the idea to apply a deformable model of an anatomical structure to the image data and to adjust the deformable model on the basis of known anatomical information of the object within the image data. In other words known anatomical features of the object to be segmented are used to adjust the deformable model in order to improve the segmentation of the selected deformable model. By means of the known anatomical features of the object, an additional parameter can be utilized for the adaption so that the segmentation becomes more reliable and more accurate and also complicated structures and structures which are badly detectable in the image data can be segmented.

In a preferred embodiment, the processing unit is designed to adapt a position of an element of the deformable model on the basis of the image data and a known position of an anatomical feature of the object. This is a possibility to adjust the deformable model to a known position so that the uncertainty is reduced and a more reliable and more accurate segmentation can be achieved.

In a preferred embodiment, the processing unit is designed to adapt a position of an element of the deformable model on the basis of the image data and a known position within the field of view of the image data. This is a possibility to add a known position to the segmentation with low technical effort, since the field of view of the image data usually comprise edge conditions which can be utilized as additional parameter for the segmentation.

In a preferred embodiment, the processing unit is designed to adapt a position of an element of the deformable model on the basis of the image data and corresponding positions in consecutive time frames of the image data. This is a possibility to utilize an anatomical feature of the object which is derivable from a known motion or a known stability of anatomical structures so that an additional parameter can be used to increase the reliability and the accuracy of the segmentation. Preferably the corresponding positions are anatomical structures, which are usually stable over time so that the respective anatomical structure can be correlated and the deformable model can be adapted accordingly.

In a preferred embodiment, the corresponding positions are known corresponding anatomical features of the object. This is a possibility to correlate anatomical features of different time frames so that a time-dependent feature can be added as additional parameter to improve the segmentation.

In a preferred embodiment, the processing unit is designed to adapt a position of an element of the deformable model on the basis of the image data and a vector or plane derived from a field of view of the image data. This is a possibility to include external information when the position is not known in all three dimensions.

In a preferred embodiment, the processing unit is designed to adapt the position of the element on the basis of a distance between the position of the element and the known position or between the corresponding positions. This is a possibility to reduce the technical effort for adapting the deformable model, since distances can be easily calculated in deformable models.

In a preferred embodiment, the deformable model is adapted to minimize a model energy comprising a spring energy derived from the distance.

In a preferred embodiment, the model energy comprises an external energy derived from the difference of the deformable model to corresponding image features in the region of interest and the spring energy. This is a possibility to combine information from the different source so that an overall improvement of the deformable model shape is achieved.

In a preferred embodiment, the spring energy is weighted by a weight factor. This is a possibility to adjust the spring energy within the overall model energy so that a balance between the different energies within the model energy can be achieved.

In a preferred embodiment, the processing unit is designed to adapt the deformable model further on the basis of an expected shape of the object. This is a possibility to improve the segmentation, since the deformable model is adapted to the medical image which includes the region of interest to be segmented.

In a preferred embodiment, the deformable model is formed by a mesh including polygons having vertices and edges. This is a possibility to achieve a segmentation with a high resolution so that the diagnosis of the anatomical structure can be improved.

In a preferred embodiment, the deformable model is adapted by adjusting the position of the vertices of the mesh. This is a possibility to adapt the deformable model with low technical effort.

As mentioned above, the present invention is based on the idea to improve the reliability and accuracy of a model-based segmentation by using external knowledge about the acquisition of the image data or anatomical structures or features to guide the segmentation. In general the anatomical features are positions of anatomical structures, anatomical distances or anatomical points, which are laterally stable over time so that additional known parameters can be added in order to reduce the uncertainty of the segmentation and to improve the reliability and accuracy of the model. The external known parameters are implemented as spring energy, which are derived from distances of points of the deformable model and corresponding points within the image data so that the deformable model can be adapted by a stepwise movement of the elements.

The overall convergence of the model adaptation can be achieved by minimizing a model energy, which is formed of an external model energy, internal model energy and the spring energy. Hence, all relevant adaptation methods can be considered so that an optimal segmentation can be achieved.

BRIEF DESCRIPTION OF THE DRAWINGS

These and other aspects of the invention will be apparent from and elucidated with reference to the embodiment(s) described hereinafter. In the following drawings

FIG. 5a, b show examples of an improved segmentation on the basis of external knowledge.

DETAILED DESCRIPTION OF THE INVENTION

Figure 1:
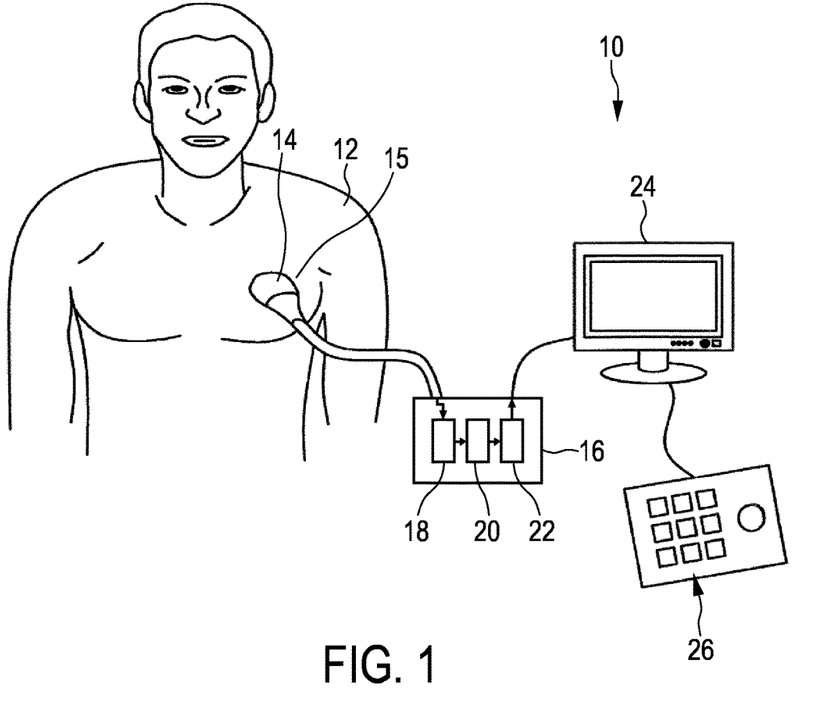
FIG. 1 shows a schematic representation of a medical imaging system in use to scan a volume of a patient's body.

FIG. 1 shows a schematic illustration of a medical imaging system 10 according to one embodiment, in particular a medical three-dimensional (3D) ultrasound imaging system 10. The medical imaging system 10 is applied to inspect a volume of an anatomical site, in particular an anatomical site of a patient 12. The medical imaging system 10 comprises an ultrasound probe 14 having at least one transducer array having a multitude of transducer elements for transmitting and/or receiving ultrasound waves. The transducer elements are preferably arranged in a two-dimensional array, in particular for providing a multi-dimensional image data.

A 3D ultrasound scan typically involves emitting ultrasound waves that illuminate a particular volume or object within the patient 12, which may be designated as target volume or region of interest 15. This can be achieved by emitting ultrasound waves at multiple different angles. A set of volume data is then obtained by receiving and processing reflected waves. The set of volume data is a representation of the region of interest 15 within the patient 12.

The medical imaging system 10 comprises an image processing apparatus 16 for providing an image via the medical imaging system 10. The image processing apparatus 16 controls the image processing that forms the image out of the echoes of the ultrasound beams received by the transducer array of the ultrasound probe 14. The image processing apparatus 16 comprises a control unit 18 that controls the acquisition of image data via the transducer array of the ultrasound probe 14 and serves as an interface 18 for receiving the image data. The control unit 18 is connected to a selection unit 20 that selects a deformable model of an anatomical structure corresponding to an object in the region of interest 15 of the image data and provides the selected deformable model and the image data to a processing unit 22 for segmenting the object in the region of interest 15 by applying the deformable model received from the selection unit 20 to the image data. After segmenting of the object within the region of interest 15, the segmentation image and the ultrasound image of the region of interest 15 may be superposed and displayed on a display screen 24. Further, an input device 26 may be provided connected to the display unit 24 or to the image processing apparatus 16 in order to control the image acquisition, the segmentation and/or the display of the ultrasound image and the segmentation results.

In an alternative embodiment, the medical imaging system 10 is connected to an MR device, a CT device or an X-ray device in order to provide corresponding medical images of the patient's body 12 which can be segmented by the image processing apparatus 16 and displayed on the display unit 24.

Figure 2:
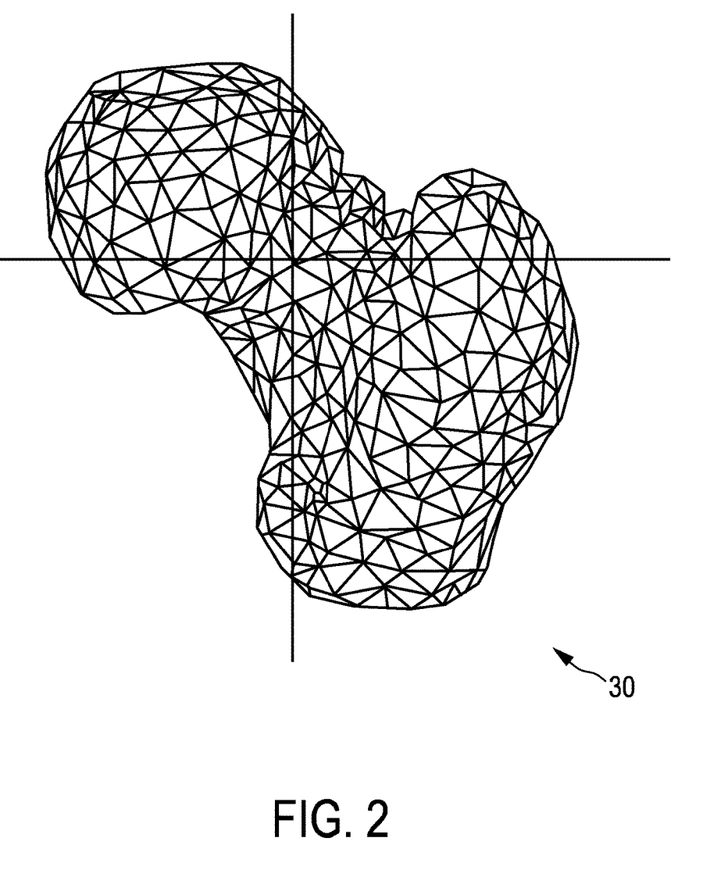
FIG. 2 shows a schematic diagram of a deformable model including polygons and vertices for segmenting a region of interest.

FIG. 2 shows a deformable model 30 that represents surfaces of an anatomical structure and their spatial constellation. The deformable model 30 is selected by the selection unit 20 and e.g. loaded from a memory of the image processing apparatus 16. The selected deformable model 30 and the image data received from the interface 18 are then provided to the processing unit 22 to adapt the deformable model to the anatomical structure identified in the image data.

The deformable model 30 is formed of a mesh comprising triangles which are formed by three neighbored vertices and a surface of the model which are connected to each other by edges. The mesh forms a surface of the anatomical structure. In an alternative embodiment, the surface of the anatomical structure can be defined by polygons replacing the triangles of the mesh.

The deformable model 30 comprises an initial spatial shape which forms a mean mesh or a shape model and the deformable model 30 is adapted to the anatomical structure within the region of interest of the image data as described in the following. In order to adapt the deformable model 30 to the anatomical structures in the region of interest 15 of the image data pattern detection of the image data is performed and the corresponding positions are correlated accordingly.

Figure 3:
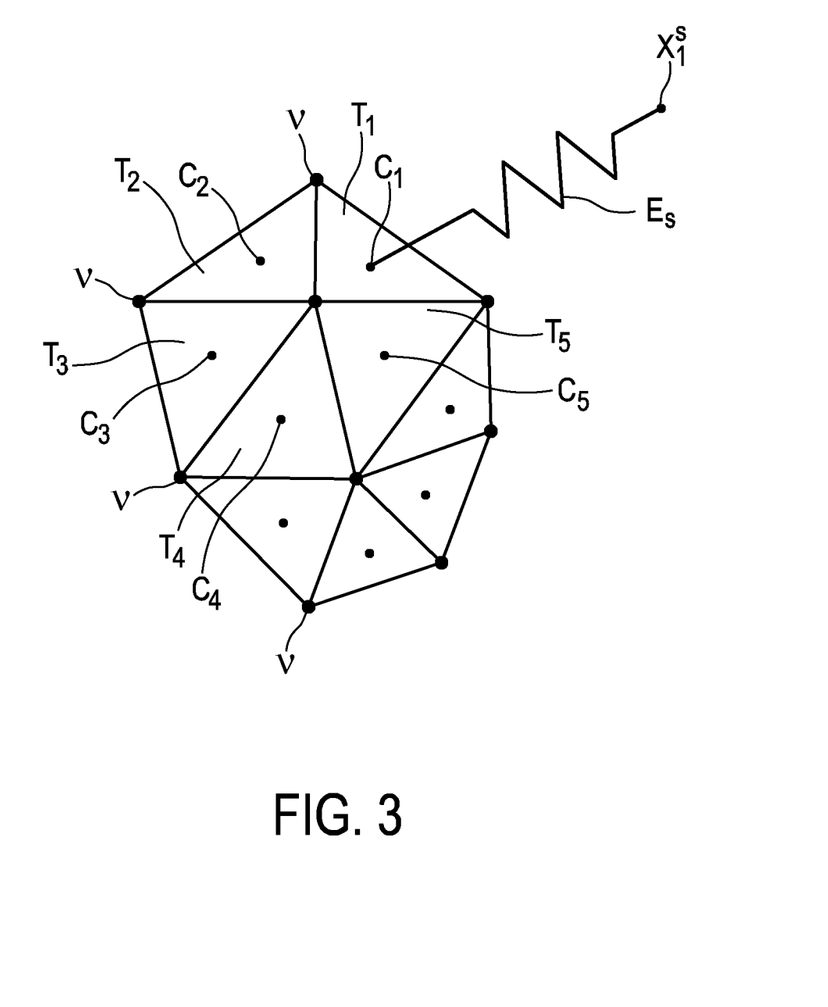
FIG. 3 shows a sectional view of the deformable model in order to explain the adaptation of the model.

FIG. 3 shows a sectional view of the deformable model 30. The deformable model 30 comprises a plurality of triangles $T_1$ to $T_5$. The triangles T are formed by vertices v, which are connected to each other by edges. Each triangle T comprises a triangle center $c_1$ to $c_5$.

After the pattern detection of the image data has been performed, the deformable model 30 is adapted to the detected anatomical structures within the image data, wherein the positions of the triangles T are adjusted so that a so-called general energy function $$E = E_{ext} + \alpha E_{int}$$

is minimized. $E_{ext}$ is in general an external energy which moves the vertices and triangles T to the corresponding positions of the anatomical structure detected in the image data by the pattern detection, wherein $E_{int}$ is an internal energy, which moves the vertices and triangles T to the original positions of the deformable model i.e. to the mean mesh or the shape model.

The external energy is calculated by $$E_{ext} = \sum_{i=1}^{T} w_i [(n_i^t)^T (c_i - x_i^t)]^2,$$

wherein $x_i^t$ is the target point found by the pattern detection, $n_i^t$ is the direction from the respective triangle T to the target point $x_i^t$ and $c_i$ is the center of the triangle $T_i$ to be adjusted to the target point $x_i^t$. The sum is formed over each of the triangles T and is each weighed by a weight factor $w_i$. When the model is adapted in a rigid of affine way by minimization of the external energy $E_{ext}$, it is also called parametric adaptation of the model 30.

The internal energy is calculated by the formula:

$$E_{int} = \sum_{i=1}^{V} \sum_{j=1}^{N(i)} [(v_i - v_j)^2 - (m_i - m_j)^2]$$

wherein v are the vertices of the adapted deformable model 30 and m are the vertices of the shape model or the mean mesh as originally provided or selected. The sum is formed over all vertices of the deformable model 30, wherein each of the distances to the neighbored vertices $v_j$ is determined. When the model is deformed freely by minimization of the external and internal energy, it is also called deformable adaptation of the deformable model 30.

The minimization of the general energy E leads to a segmentation which is a medium between the mean mesh and the detected target points determined in the image data by the pattern detection. This procedure of the adaptation of the deformable model 30 is also described in detail in EP 1 251 462 B1.

According to the invention, the deformable model 30 is also adapted on the basis of known features of the anatomical structure in order to improve the segmentation of the deformable and parametric adaptation.

The anatomical features of the anatomical structure may be a certain point or position or a distance within the image data, which is known and which can be identified. This may for example be the apex of the heart which position is generally known and which distance to the skin of the thorax is well known and can be derived from the image data due to the position of the ultrasound probe 14. Alternatively, the anatomical features of the anatomical structure may be a plane derived from the field of view with respect to the position of the ultrasound probe 14 or may be anatomical structures, which are known to be stable over time e.g. the apex of the heart so that corresponding points or positions in different time frames of the image data can be correlated. In general from the anatomical features with respect to the deformable model an additional spring energy is calculated and included in the function of the general energy E.

The additional spring energy can pull certain centers c of the triangles T to a selected point $x_j^s$ if a certain anatomical structure in the image data is identified or determined. The selection of the known anatomical structure can be performed automatically by means of the image processing apparatus 16 or may be performed manually by the user. The spring energy formed with respect to a certain selected point can be calculated by the formula:

$$E_S = \sum_{j=1}^{S} w_j [(c_j - x_j^s)]^2,$$

wherein $c_j$ are the respective centers of the triangles T, $x_j^s$ are the selected corresponding points within the image data and $w_j$ is a weight factor. In FIG. 3, the selected point $x_j^s$ is schematically shown, wherein the spring energy $E_s$ moves the center $c_1$ of the first triangle $T_1$ to the selected point $x_j^s$. Hence, the spring energy $E_s$ is calculated on the basis of the difference between the triangle centers c and the corresponding selected anatomical structure $x_j^s$ weighed by the weight factor $w_j$ to weight the three energies within the formula of the general energy.

Figure 4:
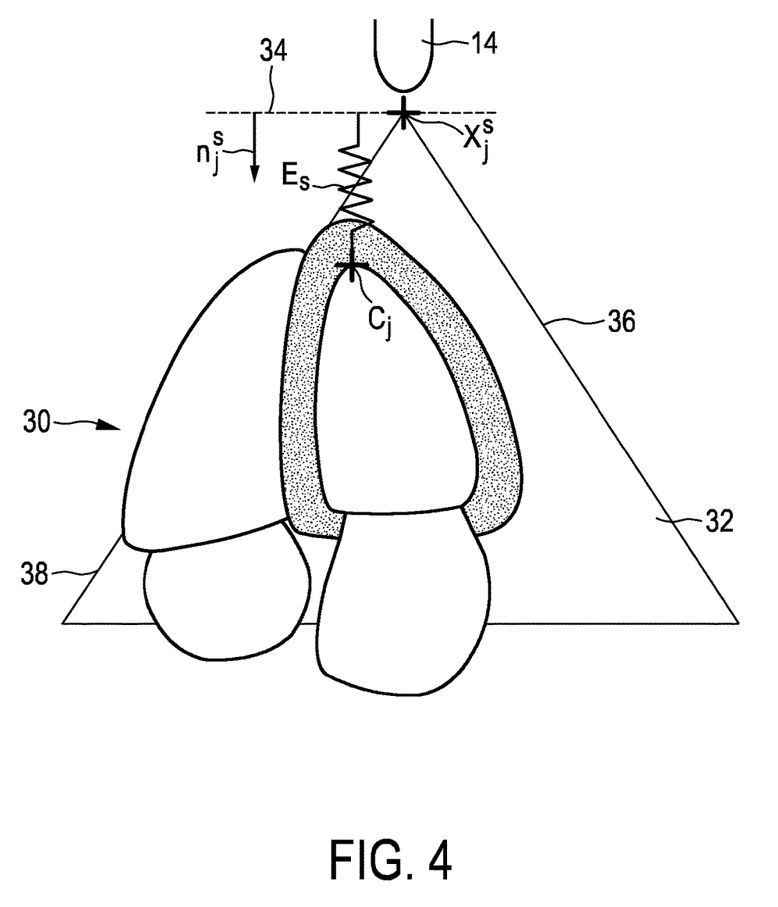
FIG. 4 shows an embodiment to adapt the deformable model on the basis of external knowledge in the field of use.

In FIG. 4 a schematic illustration of a field of view and the deformable model 30 is shown to explain an adaptation of elements of the deformable model 30 to a plane within a field of view of the medical imaging system 10. In FIG. 4 the field of view of the medical imaging system 10 and in particular of the ultrasound probe 14 is generally denoted by 32.

The anatomical structure of the object to be segmented is the heart of the patient 12 as shown in FIG. 4. In particular, the segmentation of the apex of the heart is difficult, wherein according to the present invention the distance of the apex to the tip of the ultrasound probe 14 is approximately known. The distance of the ultrasound probe 14 to the apex is known since the ultrasound probe 14 is located at the skin of the patient 12 and the anatomical distance of the apex to the skin is approximately known. In this case, the known distance of the apex can be used to adapt the deformable model 30. The target point $x_j^s$ is implemented as a plane 34 at a certain distance from the position of the ultrasound probe 14 and a direction $n_j^s$ of the triangle center $c_j$ of the apex position of the deformable model 30 to the plane 34 is determined. On the basis of these information, the spring energy $E_S$ can be determined to adapt the deformable model 30. The spring energy with respect to the plane 34 can be calculated by the formula:

$$E_S = \sum_{j=1}^{S} w_j [(n_j^s)^T (c_j - x_j^s)]^2,$$

wherein $n_j^s$ is the direction to the plane 34, $c_j$ the center of the triangle of the deformable model 30 to be adapted and $x_j^s$ the target point at which the anatomical structure is actually located. The so determined spring energy $E_S$ pulls the apex $c_j$ of the deformable model 30 to the plane 34. In this case, the position of the ultrasound probe 14 is estimated as the intersection of the two border rays 36, 38 describing the frustum of the field of view in the center slice.

In a further embodiment, the position of a certain element of the deformable model 30 in different time frames of the image data is used. Certain anatomical structures, in particular the apex of the heart are spatially stable within a cardiacal cycle so that the position of the apex within the deformable models 30 in different time frame of the image data can be used to adapt the deformable model 30.

In this case different time frames are segmented together and a spring energy is calculated on the basis of a distance of the corresponding elements of the deformable model 30, in particular on the basis of the distance of the triangle centers $c_j$ between the different time frames of the image data. The time-dependent spring energy to adapt the deformable model 30 is calculated by the formula:

$$E_S = \sum_{j=1}^{S} w_j (c_{j,t1} - c_{j,t2})^2,$$

wherein $c_{j,t1}$ and $c_{j,t2}$ are the triangle centers $c_j$ of the different time frames t1 and t2, wherein $w_j$ is a weight factor. If the position of the triangle centers $c_j$ in the different time frames t1, t2 have a large difference, the time-dependent spring energy $E_s$ is high and the respective triangles of the deformable model 30 are adapted accordingly in order to reduce the spring energy $E_s$.

It shall be understood that not only a spatially stable anatomical structure can be used to adapt the deformable model to improve the segmentation also a known motion of anatomical structure within a cycle so that the general anatomical behavior of the object to be segmented can be used as additional formation.

The general energy E of the deformable model to be minimized during the adaptation can be calculated by means of the formula:

$$E = E_{ext} + \alpha E_{int} + E_S.$$

Figure 5:
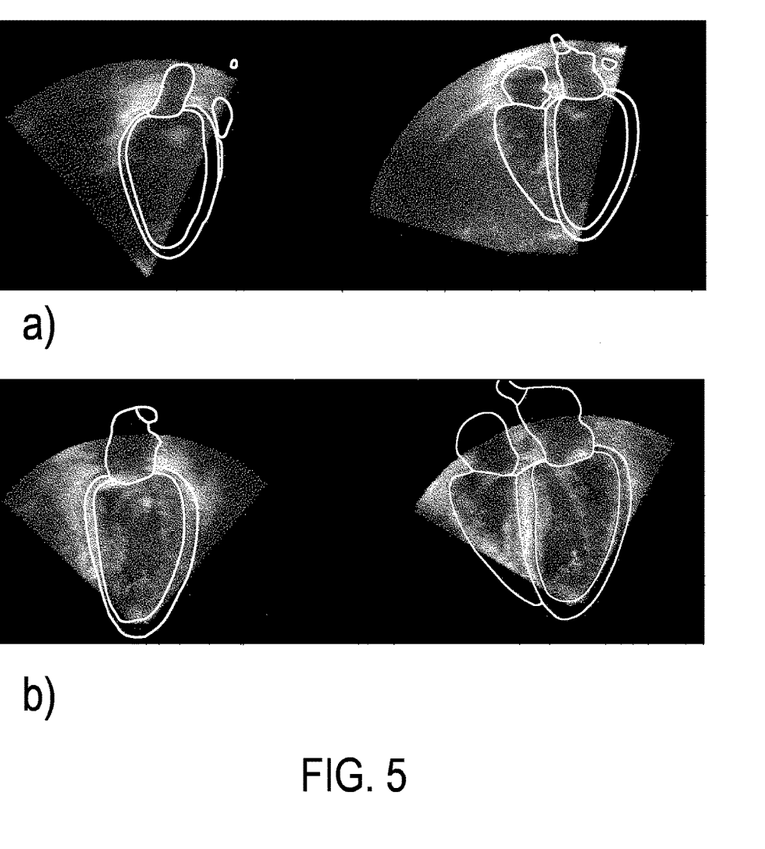

The additional spring energy and the additional information regarding the anatomical features of the object can improve the segmentation of the field of view 52, in particular the segmentation of the apex of the heart. This is in particular useful if the apex is not visible in the image data received from the ultrasound probe 14. The resulting segmentations of the heart improved on the basis of the additional anatomical information are shown in FIG. 5a, b. It has been shown that the additional anatomical information can improve the volume quantification in particular of the left ventricle in end-diastolic and end-systolic images so that the overall diagnostic reliability can be improved.

Figure 6:
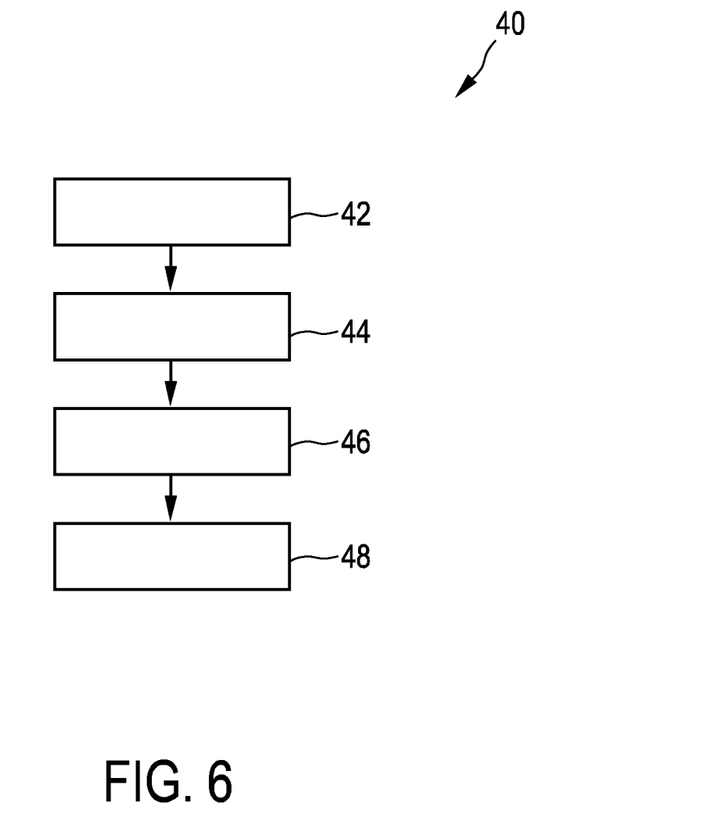
FIG. 6 shows a flow diagram of a method for segmenting a region of interest.

FIG. 6 shows a schematic flow diagram illustrating the method for segmenting the region of interest in the multi-dimensional image data of the patient 12. The method is generally denoted by 40.

The method 40 starts with the acquisition of the image data by means of the ultrasound probe 14 and with the receiving of the image data by means of the interface 18 of the image processing apparatus 16 shown at step 42. After receiving the image data the deformable model 30 is selected by the selection unit 20 corresponding to the anatomical structure of the object in the region of interest 15 to be segmented as shown in step 44. The deformable model 30 is selected from a memory of the processing apparatus 16. After the selection at step 44 the region of interest 15 is segmented by applying the deformable model 30 to the image data as shown in step 46. The deformable model 30 is finally adapted on the basis of known features of the object in the image data as shown at step 48.

In step 48, the deformable model 30 may be further adapted on the basis of the image features determined by a pattern detection and on the basis of the mean mesh of the deformable model as originally selected in order to minimize the general energy E as described above.

It shall be understood that the image processing apparatus 16 can be formed as a computer program carried out on a computer and that the method 40 can be carried out by the computer program.

The computer program may be stored/distributed on a suitable (non-transitory) medium, such as an optical storage medium or a solid-state medium supplied together with or as part of other hardware, but may also be distributed in other forms, such as via the Internet or other wired or wireless telecommunication systems. Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution device.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An image processing apparatus for segmenting a region of interest in multi-dimensional image data of an object, comprising:
   a memory storing a deformable mesh model of an anatomical structure corresponding to the object in the image data;
   an interface configured to couple the image processing apparatus to a source of the image data of the object including the region of interest to be segmented; and
   a processing unit configured to receive, via the interface, the image data and to segment the region of interest by adapting a position of an element of the deformable mesh model to the anatomical structure identified in the image data and a distance between the element and a known position of an anatomical feature of the object, wherein the processing unit is configured to adapt the deformable mesh model to minimize a model energy comprising a spring energy derived from the distance.

2. The image processing apparatus as claimed in claim 1, wherein the processing unit is configured to adapt a position of an element of the deformable mesh model on the basis of the image data and a known position within a field of view of the image data.

3. The image processing apparatus as claimed in claim 1, wherein the processing unit is configured to adapt a position of an element of the deformable mesh model on the basis of the image data and corresponding positions in consecutive time frames of the image data.

4. The image processing apparatus as claimed in claim 1, wherein the processing unit is configured to adapt a position of an element of the deformable mesh model on the basis of the image data and a vector or plane derived from a field of view of the image data.

5. The image processing apparatus as claimed in claim 3, wherein the corresponding positions are known corresponding anatomical features of the object.

6. The image processing apparatus as claimed in claim 1, wherein the model energy comprises an external energy derived from the difference of the deformable mesh model to corresponding image features in the region of interest and the spring energy.

7. The image processing apparatus as claimed in claim 6, wherein the spring energy is weighted by a weight factor.

8. The image processing apparatus as claimed in claim 1, wherein the processing unit is configured to adapt the deformable mesh model on the basis of an expected shape of the object.

9. The image processing apparatus as claimed in claim 1, wherein the deformable mesh model comprises polygons having vertices and edges.

10. The image processing apparatus as claimed in claim 9, wherein the deformable mesh model is adapted by adjusting the position of the vertices of the polygons.

11. A method for segmenting a region of interest in a multi-dimensional image data of an object, comprising the steps of:

storing a deformable mesh model of an anatomical structure corresponding to the object in the image data;

coupling the image processing apparatus to a source of the image data of the object including the region of interest to be segmented, receiving the image data and segmenting the region of interest by adapting a position of an element of the deformable mesh model to the anatomical structure identified in the image data and a distance between the element and a known position of an anatomical feature of the object, wherein adapting the deformable mesh model minimizes a model energy comprising a spring energy derived from the distance.

12. A computer program for segmenting a region of interest in multi-dimensional image data of an object comprising program code means for causing a computer to carry out the steps:

storing a deformable mesh model of an anatomical structure corresponding to the object in the image data;

coupling the image processing apparatus to a source of the image data of the object including the region of interest to be segmented, receiving the image data and segmenting the region of interest by adapting a position of an element of the deformable mesh model to the anatomical structure identified in the image data and a distance between the element and a known position of an anatomical feature of the object, when said computer program is carried out on a computer, wherein adapting the deformable mesh model minimizes a model energy comprising a spring energy derived from the distance.

* * * * *